(12) United States Patent
Remlinger et al.

(10) Patent No.: US 11,826,490 B1
(45) Date of Patent: Nov. 28, 2023

(54) EXTRACELLULAR MATRIX SHEET DEVICES WITH IMPROVED MECHANICAL PROPERTIES AND METHOD OF MAKING

(71) Applicant: ACell, Inc., Columbia, MD (US)

(72) Inventors: Nathaniel Remlinger, Baltimore, MD (US); Luai Huleihel, Baltimore, MD (US); Jiayu Tang, Sunnyvale, CA (US)

(73) Assignee: ACell, Inc., Columbia, MD (US)

( * ) Notice: Subject to any disclaimer, the term of this patent is extended or adjusted under 35 U.S.C. 154(b) by 117 days.

(21) Appl. No.: 17/554,105

(22) Filed: Dec. 17, 2021

Related U.S. Application Data

(60) Provisional application No. 63/131,600, filed on Dec. 29, 2020.

(51) Int. Cl.
| | |
|---|---|
| A61L 27/36 | (2006.01) |
| A61K 9/70 | (2006.01) |
| A61K 35/12 | (2015.01) |
| A61K 35/34 | (2015.01) |

(52) U.S. Cl.
CPC ............ *A61L 27/3683* (2013.01); *A61K 9/70* (2013.01); *A61K 35/12* (2013.01); *A61K 35/34* (2013.01); *A61L 27/3633* (2013.01); *A61L 27/3691* (2013.01); *A61L 2300/64* (2013.01)

(58) Field of Classification Search
CPC .............................. A61L 27/3683; A61K 9/70
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 4,978,668 A | 12/1990 | Babbs et al. | |
| 5,007,927 A | 4/1991 | Badylak et al. | |
| 5,275,826 A | 1/1994 | Badylak et al. | |
| 5,281,422 A | 1/1994 | Badylak et al. | |
| 5,354,274 A | 10/1994 | Demeter et al. | |
| 5,372,821 A | 12/1994 | Badylak et al. | |
| 5,445,833 A | 8/1995 | Badylak et al. | |
| 5,516,533 A | 5/1996 | Badylak et al. | |
| 5,554,389 A | 9/1996 | Badylak et al. | |
| 5,573,784 A | 11/1996 | Badylak et al. | |
| 5,641,518 A | 6/1997 | Badylak et al. | |
| 5,645,860 A | 7/1997 | Knapp et al. | |
| 5,695,998 A | 12/1997 | Badylak et al. | |
| 5,711,969 A | 1/1998 | Patel et al. | |
| 5,753,267 A | 5/1998 | Badylak et al. | |
| 5,755,791 A | 5/1998 | Whitson et al. | |
| 5,762,966 A | 6/1998 | Knapp et al. | |
| 5,866,414 A | 2/1999 | Badylak et al. | |
| 5,885,619 A | 3/1999 | Patel et al. | |
| 5,955,110 A | 9/1999 | Patel et al. | |
| 5,968,096 A | 10/1999 | Whitson et al. | |
| 5,997,575 A | 12/1999 | Whitson et al. | |
| 6,096,347 A | 8/2000 | Geddes et al. | |
| 6,099,567 A | 8/2000 | Badylak et al. | |
| 6,126,686 A | 10/2000 | Badylak et al. | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,331,319 B1 | 12/2001 | Badylak et al. | |
| 6,358,284 B1 | 3/2002 | Fearnot et al. | |
| 6,375,989 B1 | 4/2002 | Badylak et al. | |
| 6,379,710 B1 | 4/2002 | Badylak et al. | |
| 6,475,232 B1 | 11/2002 | Babbs et al. | |
| 6,485,723 B1 | 11/2002 | Badylak et al. | |
| 6,576,265 B1 | 6/2003 | Spievack | |
| 6,579,538 B1 | 6/2003 | Spievack | |
| 6,653,291 B1 | 11/2003 | Badylak et al. | |
| 6,696,074 B2 | 2/2004 | Dai et al. | |
| 6,696,270 B2 | 2/2004 | Badylak et al. | |
| 6,783,776 B2 | 8/2004 | Spievack | |
| 6,793,939 B2 | 9/2004 | Badylak et al. | |
| 6,849,273 B2 | 2/2005 | Spievack | |
| 6,852,339 B2 | 2/2005 | Spievack | |
| 6,861,074 B2 | 3/2005 | Spievack | |
| 6,869,619 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 6,969,523 B1 | 11/2005 | Mattern et al. | |
| 7,087,089 B2 | 8/2006 | Patel et al. | |
| 7,354,702 B2 | 4/2008 | Dai et al. | |
| 7,452,371 B2 | 11/2008 | Pavcnik et al. | |
| 7,485,138 B2 | 2/2009 | Fearnot et al. | |
| 7,597,710 B2 | 10/2009 | Obermiller | |
| 7,652,077 B2 | 1/2010 | Cook et al. | |
| 7,745,217 B2 | 6/2010 | Patel et al. | |
| 7,771,717 B2 | 8/2010 | Badylak et al. | |
| 7,776,596 B2 | 8/2010 | Badylak et al. | |
| 7,795,022 B2 | 9/2010 | Badylak et al. | |
| 7,795,027 B2 | 9/2010 | Hiles | |
| 7,815,923 B2 | 10/2010 | Johnson et al. | |

(Continued)

OTHER PUBLICATIONS

US 7,608,454 B2, 10/2009, Badylak et al. (withdrawn)

*Primary Examiner* — Emily A Cordas
*Assistant Examiner* — Maytee Marie Contes De Jesus
(74) *Attorney, Agent, or Firm* — Eva Tan

(57) ABSTRACT

Described are devices and associated methods of producing extracellular matrix (ECM) sheet devices with strengthened mechanical properties due to the selective retention of muscle tissue layers during processing.

20 Claims, 4 Drawing Sheets

(56) References Cited

U.S. PATENT DOCUMENTS

| | | |
|---|---|---|
| 7,897,167 B2 | 3/2011 | Armstrong et al. |
| 7,914,567 B2 | 3/2011 | Pavcnik et al. |
| 7,959,554 B2 | 6/2011 | McAlexander et al. |
| 7,993,679 B2 | 8/2011 | Ingram et al. |
| 8,187,619 B2 | 5/2012 | Johnson |
| 8,192,763 B2 | 6/2012 | Johnson |
| 8,211,168 B2 | 7/2012 | Purdy et al. |
| 8,298,586 B2 | 10/2012 | Bosley et al. |
| 8,357,402 B2 | 1/2013 | Ingram et al. |
| 8,409,625 B2 | 4/2013 | Badylak et al. |
| 8,444,687 B2 | 5/2013 | Pavcnik et al. |
| 8,454,678 B2 | 6/2013 | Hiles |
| 8,455,008 B2 | 6/2013 | Johnson |
| 8,535,349 B2 | 9/2013 | Chen et al. |
| 8,541,032 B2 | 9/2013 | Bosley et al. |
| 8,541,372 B2 | 9/2013 | Shah et al. |
| 8,557,277 B2 | 10/2013 | Virkler et al. |
| 8,591,930 B2 | 11/2013 | Hiles et al. |
| 8,647,677 B2 | 2/2014 | Badylak et al. |
| 8,652,191 B2 | 2/2014 | Fearnot et al. |
| 8,652,500 B2 | 2/2014 | Bosley et al. |
| 8,658,196 B2 | 2/2014 | Janis |
| 8,663,086 B2 | 3/2014 | Duncan et al. |
| 8,716,227 B2 | 5/2014 | Cook et al. |
| 8,741,352 B2 | 6/2014 | Hodde et al. |
| 8,784,889 B2 | 7/2014 | Hodde et al. |
| 8,790,414 B2 | 7/2014 | O'Brien et al. |
| 8,802,436 B1 | 8/2014 | Kentner et al. |
| 8,808,352 B2 | 8/2014 | Eells et al. |
| 8,835,174 B2 | 9/2014 | Fette et al. |
| 8,840,917 B2 | 9/2014 | Armstrong et al. |
| 8,846,060 B2 | 9/2014 | Archibald et al. |
| 8,895,304 B2 | 11/2014 | Ette et al. |
| 8,915,941 B2 | 12/2014 | Obermiller et al. |
| 8,927,003 B2 | 1/2015 | Badylak et al. |
| 8,932,805 B1 | 1/2015 | Brahm |
| 8,962,035 B2 | 2/2015 | Bosley et al. |
| 8,968,761 B2 | 3/2015 | Bosley et al. |
| 8,975,075 B2 | 3/2015 | Fette et al. |
| 9,011,895 B2 | 4/2015 | Dai et al. |
| 9,044,455 B2 | 6/2015 | Shah et al. |
| 9,056,078 B2 | 6/2015 | Bosley et al. |
| 9,084,722 B2 | 7/2015 | Gilbert et al. |
| 9,113,851 B2 | 8/2015 | Agnew |
| 9,119,831 B2 | 9/2015 | Kentner et al. |
| 9,138,445 B2 | 9/2015 | Hodde |
| 9,149,262 B2 | 10/2015 | Obermiller et al. |
| 9,186,435 B2 | 11/2015 | Hiles |
| 9,226,736 B2 | 1/2016 | Obermiller et al. |
| 9,238,091 B2 | 1/2016 | Kentner et al. |
| 9,254,188 B2 | 2/2016 | Dempsey |
| 9,265,860 B2 | 2/2016 | Spievack |
| 9,295,757 B2 | 3/2016 | Patel et al. |
| 9,404,077 B2 | 8/2016 | Fette et al. |
| 9,433,701 B2 | 9/2016 | Spievack |
| 9,456,813 B2 | 10/2016 | Obermiller et al. |
| 9,456,815 B2 | 10/2016 | Armstrong et al. |
| 9,474,514 B2 | 10/2016 | Agnew et al. |
| 9,474,829 B2 | 10/2016 | Kentner et al. |
| 9,480,771 B2 | 11/2016 | Fette et al. |
| 9,492,149 B2 | 11/2016 | Obermiller et al. |
| 9,492,267 B2 | 11/2016 | Hiles |
| 9,498,327 B1 | 11/2016 | Brahm |
| 9,504,769 B2 | 11/2016 | Hiles et al. |
| 9,538,996 B2 | 1/2017 | Patel et al. |
| 9,561,307 B2 | 2/2017 | Bosley et al. |
| 9,572,556 B2 | 2/2017 | Obermiller et al. |
| 9,579,183 B2 | 2/2017 | Bosley et al. |
| 9,585,983 B1 | 3/2017 | Brahm |
| 9,687,215 B2 | 6/2017 | Obermiller et al. |
| 9,764,056 B2 | 9/2017 | Fette et al. |
| 9,788,821 B2 | 10/2017 | Johnson et al. |
| 9,789,138 B1 | 10/2017 | Brahm et al. |
| 9,795,638 B1 | 10/2017 | Brahm |
| 9,795,639 B1 | 10/2017 | Brahm |
| 9,795,713 B2 | 10/2017 | Kentner et al. |
| 9,839,721 B2 | 12/2017 | Mohan et al. |
| 9,855,301 B1 | 1/2018 | Brahm |
| 9,861,517 B2 | 1/2018 | Pavcnik et al. |
| 9,919,078 B1 | 3/2018 | Brahm |
| 9,931,439 B2 | 4/2018 | Fearnot et al. |
| 9,956,315 B2 | 5/2018 | Patel et al. |
| 9,993,506 B2 | 6/2018 | Brahm |
| 9,999,707 B2 | 6/2018 | Gilbert et al. |
| 10,010,659 B1 | 7/2018 | Brahm et al. |
| 10,016,459 B1 | 7/2018 | Brahm |
| 10,071,187 B2 | 9/2018 | Hiles et al. |
| 10,092,678 B2 | 10/2018 | Spievack |
| 10,245,349 B2 | 4/2019 | Brahm |
| 10,265,438 B1 | 4/2019 | Brahm |
| 10,342,523 B2 | 7/2019 | Obermiller et al. |
| 10,470,749 B2 | 11/2019 | Obermiller et al. |
| 10,471,182 B2 | 11/2019 | Hiles et al. |
| 10,500,309 B2 | 12/2019 | Shah et al. |
| 10,517,994 B2 | 12/2019 | Bosley et al. |
| 10,555,974 B1 | 2/2020 | Brahm |
| 10,568,914 B1 | 2/2020 | Brahm |
| 10,688,219 B2 | 6/2020 | Patel et al. |
| 10,786,600 B1 | 9/2020 | Brahm |
| 10,806,833 B1 | 10/2020 | Pomrink et al. |
| 10,898,610 B2 | 1/2021 | Bosley et al. |
| 10,905,798 B1 | 2/2021 | Brahm |
| 10,905,800 B1 | 2/2021 | Brahm |
| 11,000,628 B2 | 5/2021 | Bosley et al. |
| 11,013,829 B2 | 5/2021 | Bosley et al. |
| 11,026,667 B2 | 6/2021 | Agnew et al. |
| 11,064,987 B2 | 7/2021 | Obermiller et al. |
| 11,065,368 B2 | 7/2021 | Peck et al. |
| 11,077,229 B1 | 8/2021 | Brahm |
| 11,077,231 B2 | 8/2021 | Hiles et al. |
| 11,167,061 B1 | 11/2021 | Brahm |
| 11,173,231 B2 | 11/2021 | Hiles et al. |
| 11,185,611 B2 | 11/2021 | Gilbert et al. |
| 11,224,616 B1 | 1/2022 | Brahm |
| 11,224,617 B1 | 1/2022 | Brahm |
| 2004/0043006 A1 | 3/2004 | Badylak et al. |
| 2004/0078076 A1 | 4/2004 | Badylak et al. |
| 2004/0187877 A1 | 9/2004 | Badylak et al. |
| 2005/0143807 A1 | 6/2005 | Pavcnik et al. |
| 2005/0182484 A1 | 8/2005 | Patel et al. |
| 2006/0136047 A1 | 6/2006 | Obermiller et al. |
| 2006/0251702 A1 | 11/2006 | Janis et al. |
| 2007/0166395 A1* | 7/2007 | McAlexander ..... A61L 27/3629 424/551 |
| 2007/0179507 A1 | 8/2007 | Shah |
| 2007/0184122 A1 | 8/2007 | Johnson et al. |
| 2008/0167728 A1 | 7/2008 | Cook et al. |
| 2009/0318934 A1 | 12/2009 | Johnson et al. |
| 2011/0060362 A1 | 3/2011 | Patel et al. |
| 2015/0258142 A1* | 9/2015 | Dhanaraj ............ A61L 27/3633 424/572 |
| 2016/0089477 A1 | 3/2016 | Valmikinathan et al. |
| 2016/0206785 A1 | 7/2016 | Patel et al. |
| 2017/0072099 A1 | 3/2017 | Hiles et al. |
| 2017/0086808 A1 | 3/2017 | Patel et al. |
| 2018/0036451 A1 | 2/2018 | Fette et al. |
| 2018/0043057 A1 | 2/2018 | Kentner et al. |
| 2018/0228939 A1 | 8/2018 | Hiles et al. |
| 2018/0280574 A1 | 10/2018 | Gilbert et al. |
| 2019/0046211 A1 | 2/2019 | Bronikowski et al. |
| 2019/0336650 A1 | 11/2019 | Hiles et al. |
| 2020/0129666 A1 | 4/2020 | Bosley et al. |
| 2020/0188559 A1 | 6/2020 | Hiles et al. |
| 2020/0316257 A1 | 10/2020 | Patel et al. |
| 2021/0077661 A1 | 3/2021 | Valmikinathan et al. |
| 2021/0308342 A1 | 10/2021 | Peck et al. |

\* cited by examiner

EXTRACELLULAR MATRIX SHEET DEVICES WITH IMPROVED MECHANICAL PROPERTIES AND METHOD OF MAKING

CROSS-REFERENCE TO RELATED APPLICATIONS

This application claims priority to and benefit under 35 U.S.C. 119(e) to U.S. Provisional Application No. 63/131,600, filed Dec. 29, 2020, the entire contents of which are incorporated by reference herein.

BACKGROUND

Submucosal tissues of warm-blooded vertebrates are useful in tissue grafting materials and have an extensive history of use in surgical applications. In particular, submucosal tissue graft compositions derived from extracellular matrices (ECM), such as urinary bladders, have been described in U.S. Pat. Nos. 5,554,389 and 6,576,265, both incorporated herein by reference. ECM sheet devices are fully-resorbable devices and mitigate the inflammatory response. Importantly, the lack of cross-linking in ECM sheet scaffolds, in contrast to synthetic scaffolds, encourages the repair and remodeling response of damaged tissues post-implantation.

Although ECM devices offer a number of advantages in wound care, physicians are accustomed to working with stronger, permanent devices, such as nylon meshes and polytetrafluoroethylene (PTFE), in surgical applications where suture-retention strength is critical, and are hesitant to use biodegradable ECM devices due to their weaker mechanical properties.

The development of ECM sheet layering has been sufficient to increase the mechanical strength of ECM devices. However, multiple layers in ECM devices decreases the conformability of the ECM device to the underlying tissue at the surgical site. Therefore, a need persists for enhanced, resorbable, ECM sheet devices with strengthened mechanical properties.

SUMMARY

The present disclosure describes the selective retention of muscle tissue during ECM processing, either uniformly or regionally across the entire ECM device to increase mechanical strength and decrease failure rates during surgical and wound healing applications. ECM sheet devices allow for better surgical outcomes than permanent scaffolds, due to their mimicry of mammalian tissue during the wound repair response. Stronger ECM devices also permit ECM to be used in additional surgical applications, such as suture retention strength and to correct bridging defects, which require higher mechanical strength.

To produce extant ECM devices, mammalian tissues are skinned, removing the epithelial layer, and delaminated removing the majority of the muscle tissue.

In contrast, in some embodiments of the present disclosure, the mammalian tissue is not delaminated and the resulting ECM retains residual muscle tissue, enabling ECM devices to retain mechanical strength.

In some embodiments, to retain residual muscle tissue during urinary bladder matrix (UBM) production, harvested porcine bladders go through thawing and preparation, and are subsequently skinned, but do not undergo muscle delamination. In fact, production of UBM from bladders in which the muscle layers were not delaminated was shown to be more time and material efficient and generated less waste than production of UBM in which the muscle tissue was delaminated. Retention of muscle tissue in UBM is also advantageous in that it does not require the use of new reagents, chemical, or additives.

To produce ECM sheets, tissues may also undergo differential scraping in specific regions of the sheet. ECM that are differentially scraped can be layered onto muscle-delaminated ECM sheets, other differentially scraped ECM, or ECM retaining residual muscle tissue. Subsequent processing such as disinfection, decellularization, and lamination occur after the sheet device is configured.

ECM sheets retaining muscle tissue may also be cut into desired reinforcement shapes, such as a frame or strips to reinforce the ECM device as needed for a tissue healing application. These ECM shapes may be layered onto other ECM sheets during the lamination process in order to create the final ECM sheet devices.

In examples, extracellular matrix (ECM) sheet compositions of the present disclosure include at least a decellularized basement membrane, lamina propria, and muscle tissue, wherein an ECM sheet is differentially scraped of the muscle tissue. In some examples, the ECM sheet is layered or stacked with at least one additional ECM sheet.

In some examples, the at least one additional ECM sheet is selected from the group of muscle delaminated ECM sheets, additional differentially scraped ECM sheets, and ECM sheets wherein the residual muscle tissue is fully retained.

In further examples, the ECM sheet is cut into reinforcement shapes, optionally wherein the shapes are frames and/or strips, optionally wherein the frames and/or strips are differentially scraped of muscle tissue in a width of at least 0.1%, 1.0%, 5%, 10%, or 50% of the ECM sheet long-axis diameter, optionally wherein the ECM sheets are scraped of muscle tissue in a pattern selected from the group comprising a straight line, a diagonal line, cross-hatching pattern, and/or circular patterns, optionally wherein the scraping pattern contributes increased mechanical strength to the ECM.

In some examples, the ECM sheets are stacked or staggered in configurations of at least 2, 3, 4, 5, 6, 7, 8, 9, 10, 11, 12, 13, 14, 15 16, 17, 18, 19 or 20 layers.

In further examples, the one or more ECM sheets is derived from one or more of the following mammalian tissues: urinary bladder matrix (UBM), small intestine submucosa (SIS), spleen, liver, lung, heart, pancreas, ovary, forestomach, and dermis.

In some examples, the ECM sheet composition comprises at least two muscle delaminated ECM sheets on the top and bottom of the sheet stack, and the composition further comprises at least one differentially scraped ECM sheet or strip.

Examples of a method of making an extracellular matrix (ECM) sheet composition of the present disclosure include removing the surface epithelium of a mammalian tissue to form a de-cellularized tissue having an epithelial basement membrane, lamina propria, and muscle tissue, and scraping the muscle tissue into a pattern.

In further examples, the method of making the ECM sheet composition of the present disclosure provides increased mechanical strength relative to ECM sheet compositions containing no muscle tissue. In some examples, the method of making the ECM sheet composition includes stacking or staggering ECM sheets in configurations of at least 2, 3, 4, 5, 6, 7, 8, 9, 10, 11, 12, 13, 14, 15, 16, 17, 18, 19 or 20 layers. In some examples, the method of making further includes vacuum drying, lyophilization, vacuum pressing and/or air drying. In some examples, the method of making the ECM sheet compositions employs mammalian urinary bladder matrix (IJBM), small intestine submucosa (SIS), spleen, liver, lung, heart, pancreas, ovary, forestomach and/or dermis.

Examples of a method of repairing defects of mammalian tissue of the present disclosure include applying one or more ECM sheet compositions differentially scraped of muscle tissue to a mammalian subject, optionally as a treatment for wound healing, and/or in surgical applications. In example, two or more ECM sheets that are layered and laminated may be scraped of muscle tissue in the same scraping pattern and/or extent or in different scraping patterns and/or extents.

BRIEF DESCRIPTION OF THE DRAWINGS

Reference to the detailed description, in conjunction with the following figures, will make the disclosure more fully understood, wherein:

FIG. 5A is a graph demonstrating the relative tensile strength of delaminated UBM sheet devices versus muscle-retaining UBM sheet devices in 3 and 6 layer configurations. FIG. 5B is a graph demonstrating the relative suture retention strength of delaminated UBM sheet devices versus muscle-retaining UBM sheet devices in 3 and 6 layer configurations. FIG. 5C is a graph demonstrating the relative tissue thickness of delaminated UBM sheet devices versus muscle-retaining UBM sheet devices in 3 and 6 layer configurations.

DETAILED DESCRIPTION

Figure 1:
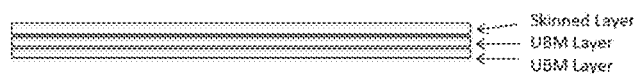
FIG. 1 illustrates a representative configuration of ECM sheets, e.g. Urinary Bladder Matrix (UBM) sheets in a 3-layer stacking configuration.

In the description that follows, like components have the same reference numerals, regardless of whether they present in different examples. To illustrate examples in a clear and concise manner, the drawings may not necessarily illustrate scale and may show certain features in somewhat schematic form. Features described and/or illustrated with respect to one example may exist in the same way or in a similar way in one or more other examples and/or in combination with or instead of the features of the other examples.

As used in the specification and claim for the purposes of describing and defining the invention, the terms "about" and "substantially" represent the inherent degree of uncertainty attributed to any quantitative comparison, value, measurement, or other representation. The terms "about" and "substantially" also represent the degree by which a quantitative representation may vary from a stated reference without resulting in a change in the basic function of the subject matter at issue. "Comprise", "include", "have," and variations of each word include the listed parts and can include additional parts not listed. "And/or" includes one or more of the listed parts and combinations of the listed parts. The terms "upper", "lower", "left", "right" and the like serve to clearly describe the disclosure but do not limit the structure, positioning and/or operation of the disclosure in any manner.

In the instant disclosure, "skinned" tissue refers to tissue wherein the superficial epithelial layer is removed. In some embodiments, the urothelial layer is removed.

In the instant disclosure, the "extracellular matrix" or "ECM" refers to mammalian tissue which has been skinned, removing the superficial epithelial layer, and which comprises at least the basement membrane and lamina propria. In some embodiments the ECM comprises residual muscle tissue including but not limited to the submucosa, the muscularis externa, and/or the tunica serosa, optionally wherein the residual muscle tissue is differentially scraped. In some embodiments the ECM is decellularized. In some embodiments, the ECM is derived from urinary bladder. In other embodiments, the ECM is derived from small intestine submucosa (SIS), spleen, liver, lung, heart, pancreas, ovary, forestomach and/or dermis.

In the instant disclosure, "delaminated" refers to full removal of muscle tissue layers including for example, the submucosa, the muscularis externa, and/or the tunica serosa.

In the instant disclosure, "decellularized" refers to removal of cells from a tissue, by any method known in the art, such as methods comprising disinfectants or acidic solutions to produce a decellularized extracellular matrix (ECM) scaffold. In some preferred embodiments, the decellularized ECM encourages the repair and remodeling of damaged tissues post-implantation.

In the instant disclosure, "basement membrane" refers to a thin, pliable sheet-like matrix, that provides cell and tissue support. The basement membrane is between epithelial tissues and the underlying connective tissue.

In the instant disclosure, "lamina propria" refers to a loose connective tissue supporting the mucosal epithelium. Compared to other loose connective tissue, lamina propria in vivo is relatively cellular.

In the instant disclosure, "muscle tissue," "muscle layers," or "muscle" refers to the smooth muscle layer in the walls of organs including but not limited to the bladder, bronchi, intestines, and blood vessels. In some embodiments the muscle tissue may include the submucosa, the muscularis externa, and/or the tunica serosa.

In the instant disclosure, "residual muscle tissue" refers to the muscle tissue remaining on mammalian-derived ECM after skinning. The residual muscle tissue may be fully (delaminated) or differentially scraped, or fully retained. In some embodiments, the residual muscle tissue provides increased mechanical strength to the ECM relative to ECM without muscle tissue. In some embodiments, the ECM comprising residual muscle tissue is derived from a urinary bladder, i.e., urinary bladder matrix (UBM). In some embodiments, the ECM is derived from small intestine submucosa (SIS), spleen, liver, lung, heart, pancreas, ovary, forestomach and/or dermis.

In the instant disclosure, "reinforcement shape" refers to cutting the ECM, optionally containing residual muscle tissue into any shape that may be then layered onto additional ECM sheets to produce an ECM sheet device. Examples include frames, strips, squares or other desired shapes. ECM in such shapes may be fully or partially scraped of residual muscle tissue.

In the instant disclosure, a "urinary bladder matrix" or "UBM" refers to a urinary bladder that is opened, stretched, and skinned wherein the superficial urothelial layer and the majority of the muscle tissue is removed, thereby leaving a residual layer of muscle tissue. The residual layer of muscle tissue is scraped into differential patterns.

In some embodiments, an "extracellular matrix sheet device," "ECM device" or "ECM sheet device" is a single ECM sheet. In some embodiments, multiple ECM sheets are stacked and/or staggered in configurations of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 layers. Multiple layers of ECM sheets may include combinations of layers that partially or fully retain muscle tissue or which contain no residual muscle tissue. For example, UBM sheet compositions of the present disclosure may comprise 3, 4, 5, 6, 7, or 8 layers of stacked or staggered skinned UBM sheets, or alternating skinned UBM sheets and laminated UBM sheets, or any other layering sequence.

In the instant disclosure, ECM sheet devices may be used to repair defects of mammalian tissue including wound healing and surgical applications. In some embodiments, ECM sheets are used to treat pressure ulcers, venous ulcers, diabetic ulcers, and/or chronic vascular ulcers. In some embodiments, ECM sheets may be used to treat tunneled or undermined wounds. In some embodiments, ECM sheets may be used to treat surgical wounds including but not limited to wounds resulting from donor sites or grafts, post-Mohs surgery, post-laser surgery, podiatric, and/or wound dehiscence. In some embodiments, ECM sheets may be used to treat trauma wounds including but not limited to abrasions, lacerations, second-degree burns, and skin tears, and draining wounds. In some embodiments, ECM sheets may be used to reinforce soft tissue during or after gastroenterological and plastic and reconstructive surgery, including but not limited to, open or laparoscopic procedures, hernia, e.g. hiatal and/or diaphragmatic, body wall repair, colon and rectal prolapse repair, tissue repair, urological repair, esophageal repair, and breast reconstruction. In some embodiments, ECM sheets may be used to minimize tissue attachment to a therapeutic device, e.g. in the case of direct contact with viscera. In some embodiments, ECM sheets may be used to treat to facilitate tissue healing in a mammal during or after surgery wherein mechanical strength is required, e.g. to repair or prevent bridging tissue defects.

In the instant disclosure, "suture retention strength" refers to the resistance of an ECM sheet against the pull-out of a suture. Resistance may be measured by pulling the suture with a constant deformation rate until pull-out of the suture from the scaffold occurs. In some embodiments, the suture strength is measured on INSTRON® tensile testing equipment.

In the instant disclosure, "stacked" and "staggered" refers to any configuration of sheets wherein the UBM sheets may overlap one another completely or partially.

In the instant disclosure, "differentially scraped" refers to scraping residual muscle tissue of an ECM sheet after skinning such that not all of the muscle tissue is removed. In some embodiments, the scraping forms a pattern. In some embodiments, the pattern is one of those embodiments A-F illustrated in FIG. 3. Exemplary patterning may include scraping any width and number of straight lines, diagonal lines, cross-hatching, circular patterns, or any variations thereof. In some embodiments, the pattern contributes increased mechanical strength uniformly and/or regionally to the UBM. In some embodiments, the width of the line scraping may be least 0.1%, at least 1.0%, at least 5%, at least 10%, or at least 50% of the sheet long-axis diameter. Some embodiments include a range of percent width of the line scraping that is a range between any two of the aforementioned percentages. In further embodiments, the percent width of the line scraping is any and all values contained within the ranges between any two of the aforementioned percentages.

In some embodiments the percent residual muscle tissue remaining on the ECM sheet after scraping is at least at least 0.01%, at least 0.1%, at least 0.5%, at least I %, at least 5%, at least 10%, at least 25%, at least 50%, at least 75%, at least 90%, or at least 99% of the residual muscle tissue present before scraping. In addition, some embodiments include a range of percent residual muscle tissue remaining on the ECM sheet that is a range between any two of the aforementioned percentages. In further embodiments, the percent residual muscle tissue remaining on the ECM sheet is any and all values contained within the ranges between any two of the aforementioned percentages.

In the instant disclosure, "dried" or "drying" of an ECM sheet refers to any method known in the art to dry ECM sheets including but not limited to vacuum drying, lyophilization, and/or air drying. In some embodiments, drying methods serve to compress the ECM sheets.

In the instant disclosure, "disinfected and rinsed" refers to ECM sheet device production wherein the ECM sheet devices are disinfected through any method known in the art, e.g. with disinfectants or acidic solutions, to rid the device of any pathogens, and subsequent rinsing of the disinfectant.

In the instant disclosure, "lamination" refers to lamination of the final ECM sheet device configuration. The term "laminate" describes both the process and the end result of two or more independent pieces of tissue bonding together. Thus, lamination produces a directed area of connection between the tissues that would not occur unless intentionally created.

FIG. 1 shows an example of a 3-layer sheet ECM device, e.g. a UBM device, comprising one "skinned" sheet, and two additional UBM sheets. Each ECM sheet may fully retain the residual muscle tissue after skinning, or be fully or partially delaminated. Stacking sheets may increase the height of the device, while in other embodiments, staggering sheets comprises partially overlapping sheets to increase the width of the device.

Figure 2:
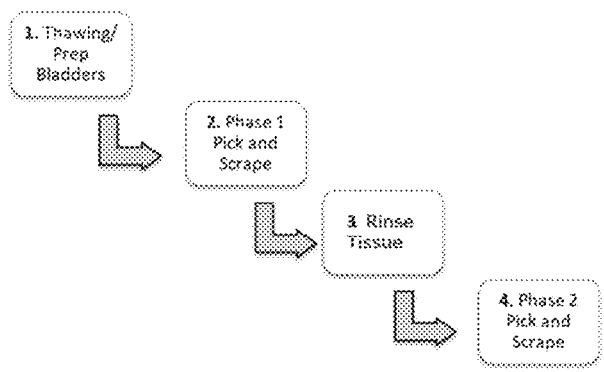
FIG. 2 is a flow chart of the manufacturing process of ECM retaining residual muscle tissue.

In FIG. 2, the manufacturing method is shown for producing ECM sheets including basement membrane and lamina propria layers. Step 2 includes skinning the ECM, and Steps 2 and 4 include physical delamination and scraping methods to remove muscle tissue. ECM of the instant disclosure may selectively retain the muscle tissue during the delamination and scraping steps.

Figure 3:
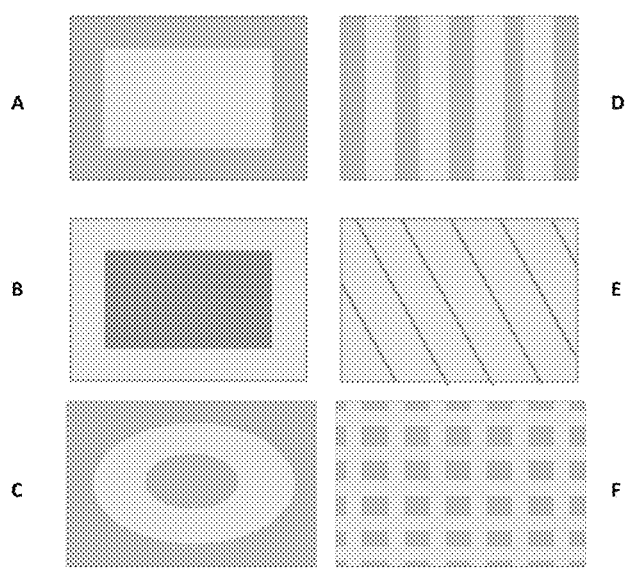
FIG. 3 illustrates representative embodiments A-F of differential scraping patterns of ECM retaining residual muscle tissue.

In FIG. 3, planar views of ECM embodiments with differential muscle tissue scraping patterns are shown, wherein the darker regions indicate zero or less scraping and the lighter regions indicate more scraping. In many embodiments, patterning may include scraping a preferred width or number of straight lines (embodiments A-C), circular, ellipse or oval patterns (embodiment D), diagonal lines (embodiment E), cross-hatching (embodiment F), or any variations thereof. The preferred pattern may depend on the desired application of the ECM device, and the spatial mechanical properties required for the application. In some embodiments, an ECM device comprising a sheet with a pattern shown in embodiment A, like a frame, may be applied in surgical applications to minimize suture pull-through.

Figure 4:
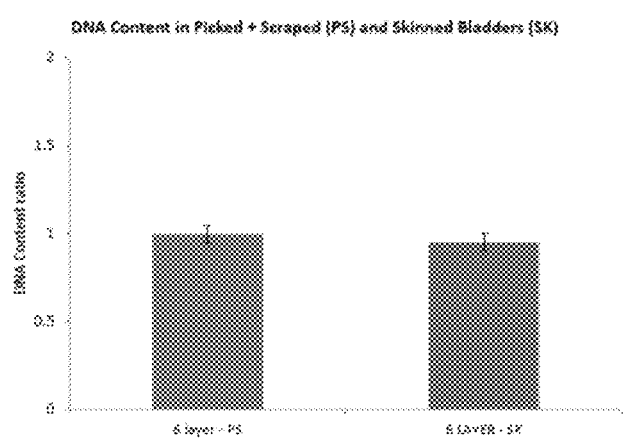
FIG. 4 is a graph of the relative DNA content of delaminated UBM ("picked and scraped") devices and UBM devices retaining residual muscle tissue ("skinned"), in 6-layer configurations.

Mechanical and DNA testing of UBM sheet configurations comprising fully delaminated sheets versus sheet configurations comprising residual muscle tissue was performed. It was found that UBM retaining residual muscle tissue did not have significantly increased DNA content compared to fully delaminated UBM, as shown by picogreen DNA assays in FIG. 4. Notably, these results indicate that decellularized UBM sheets containing residual muscle tissue are not expected to induce a pro-inflammatory response upon implantation or grafting in a mammalian patient.

Figure 5A:
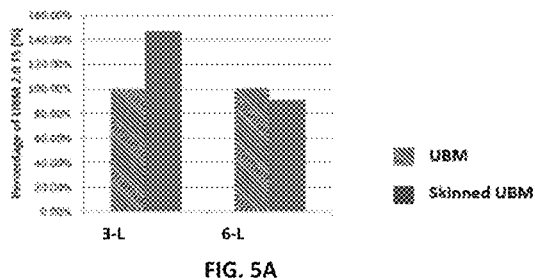
FIGS. 5A-5C compare the mechanical properties of delaminated UBM devices ("picked and scraped") and UBM devices retaining residual muscle tissue ("skinned").
Figure 5B:
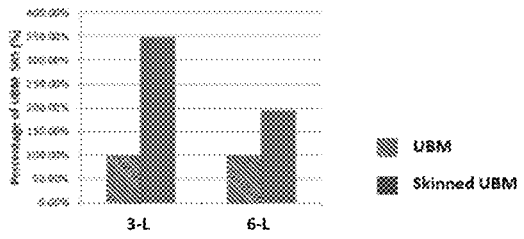
Figure 5C:
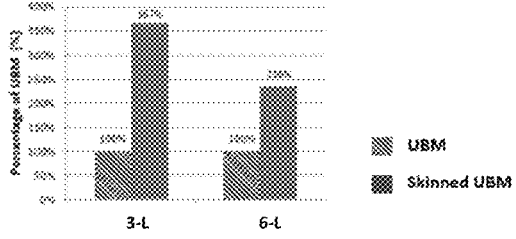

Further, although the tensile strength (FIG. 5A) did not vary linearly between the UBM devices with residual muscle tissue and those devices with fully delaminated UBM sheets, the relative suture retention strength was about 3.5-2× greater for UBM sheet devices with residual muscle tissue than for fully delaminated UBM (FIG. 5B). The thickness of the UBM sheet devices is increased with residual muscle tissue over those of the delaminated extant products (FIG. 5C).

Current UBM surgical products referred to as GENTRIX® Surgical Matrix, comprising delaminated UBM sheets are available in various configurations, including 3, 6, or 6 layers stacked and 8 layers staggered, vacuum pressed to bond the layers together. Vacuum pressing comprises compressing hydrated, remoldable material while subjecting the material to a vacuum. Vacuum pressing can laminate multiple layers of ECM material together by crushing the matrix structure of the ECM. Lyophilization may also be used to produce the final product with multiple layers. The UBM sheet compositions of the instant disclosure, wherein residual muscle tissue is retained on at least one sheet, alone and in various combinations (e.g. multiple layered, stacked and/or staggered in varying degrees and patterns) can address any suture pull through problems associated with the current products, and any other need for enhanced, resorbable, ECM sheet devices with strengthened mechanical properties.

One skilled in the art will realize the disclosure may embody other specific forms without departing from the spirit or essential characteristics thereof. The foregoing examples in all respects illustrate rather than limit the disclosure described herein. The appended claims, rather than the foregoing description, thus indicate the scope of the disclosure, and embrace all changes that come within the meaning and range of equivalency of the claims.

The invention claimed is:

1. An extracellular matrix (ECM) sheet composition, comprising: decellularized basement membrane, lamina propria, and muscle tissue, wherein an ECM sheet is differentially scraped of the muscle tissue.

2. The composition of claim 1, wherein the ECM sheet is layered or stacked with at least one additional ECM sheet.

3. The composition of claim 2, wherein the at least one additional ECM sheet is selected from the group consisting of muscle delaminated ECM sheets, differentially scraped ECM sheets, and ECM sheets wherein the residual muscle tissue is fully retained.

4. The composition of claim 1, wherein the ECM sheet is cut into reinforcement shapes selected from the group consisting of frames, strips and squares.

5. The composition of claim 4, wherein the frames or strips are differentially scraped of muscle tissue in a width of at least 0.1%, 1.0%, 5%, 10%, or 50% of the ECM sheet long-axis diameter.

6. The composition of claim 1, wherein the ECM sheet is scraped of muscle tissue in a pattern selected from the group consisting of a straight line, a diagonal line, cross-hatching pattern, and/or circular patterns.

7. The composition of claim 1, wherein the ECM sheet is scraped in a scraping pattern that contributes increased mechanical strength to the ECM.

8. The composition of claim 2, wherein the ECM sheets are stacked or staggered in configurations of at least 2, 3, 4, 5, 6, 7, 8, 9, 10, 11, 12, 13, 14, 15, 16, 17, 18, 19 or 20 layers.

9. The composition of claim 1, wherein the ECM sheet is derived from a mammalian tissue selected from the group consisting of: urinary bladder matrix (UBM), small intestine submucosa (SIS), spleen, liver, lung, heart, pancreas, ovary, forestomach and dermis.

10. The composition of claim 2, wherein the at least one additional ECM sheet is derived from a mammalian tissue selected from the group consisting of: urinary bladder matrix (UBM), small intestine submucosa (SIS), spleen, liver, lung, heart, pancreas, ovary, forestomach and dermis.

11. The composition of claim 2, comprising at least two muscle delaminated ECM sheets on the top and bottom of the sheet stack.

12. The composition of claim 11, further comprising at least one differentially scraped ECM sheet or strip.

13. A method for manufacture of an extracellular matrix (ECM) sheet composition, comprising: removing the surface epithelium of a mammalian tissue to form a decellularized tissue having an epithelial basement membrane, lamina propria, and muscle tissue, and scraping the muscle tissue into a pattern.

14. The method of claim 13, wherein the ECM sheet exhibits increased mechanical strength relative to ECM sheets containing no muscle tissue.

15. The method of claim 13, further comprising stacking or staggering ECM sheets in configurations of at least 2, 3, 4, 5, 6, 7, 8, 9, 10, 11, 12, 13, 14, 15, 16, 17, 18, 19 or 20 layers.

16. The method of claim 13, further comprising vacuum drying, lyophilization, vacuum pressing, and/or air drying the ECM sheet.

17. The method of claim 13, wherein the ECM sheet is derived from one or more mammalian tissues selected from the group consisting of: urinary bladder matrix (UBM), small intestine submucosa (SIS), spleen, liver, lung, heart, pancreas, ovary, forestomach and dermis.

18. The method of claim 15, wherein the ECM sheets are individually derived from mammalian tissue selected from the group consisting of: urinary bladder matrix (UBM), small intestine submucosa (SIS), spleen, liver, lung, heart, pancreas, ovary, forestomach and dermis.

19. A method of repairing defects of mammalian tissue comprising applying one or more ECM sheets differentially scraped of muscle tissue and comprising decellularized basement membrane, lamina propria, and muscle tissue to a mammalian subject, as a treatment for wound healing, and/or in surgical applications.

20. The method of claim 19, wherein two or more ECM sheets which are scraped of muscle tissue in the same scraping pattern or in different scraping patterns are layered and laminated.

* * * * *